United States Patent [19]

Miyake et al.

[11] Patent Number: 4,557,927
[45] Date of Patent: Dec. 10, 1985

[54] FOOD PRODUCTS AND PROCESS FOR PRODUCING SAME

[75] Inventors: Toshio Miyake, Hiromi Hijiya, both of Okayama; Shinji Suzuki, Teruo Matsumoto, both of Tokyo, all of Japan

[73] Assignee: Kabushiki Kaisha Hayashibara, Okayama, Japan

[21] Appl. No.: 582,475

[22] Filed: Feb. 22, 1984

[30] Foreign Application Priority Data

Mar. 10, 1983 [JP] Japan ................. 58-40125
Apr. 11, 1983 [JP] Japan ................. 58-64183

[51] Int. Cl.$^4$ ............ C08B 37/00; A61K 7/16; A23L 1/236
[52] U.S. Cl. ...................... 424/48; 424/49; 424/56; 424/57; 424/58; 424/64; 426/10; 435/78; 536/4.1
[58] Field of Search ........ 424/58, 48, 49, 56, 424/57, 64; 426/10; 435/78; 536/4.1

[56] References Cited

U.S. PATENT DOCUMENTS 3,963,832 6/1976 Hashimoto et al. ............ 424/58
4,219,571 8/1980 Miyake ........................ 435/78

FOREIGN PATENT DOCUMENTS 1050703 2/1959 Fed. Rep. of Germany ........ 426/10
7301275 3/1972 Netherlands ................. 426/10

OTHER PUBLICATIONS

*Up-To-Date Foodprocessing,* vol. 17, No. 9, pp. 39–47, vol. 17, No. 7, pp. 30–42 (1982).
Isao Kitagawa et al, Saponin and Sapogenol, ... XIII Structures *Chem. Pharm. Bull.,* vol. 24, No. 1, pp. 121–129 (1976).
*Up-To-Date Foodprocessing,* vol. 16, No. 5, pp. 36–40 (1981) Ohkubo et al.

*Primary Examiner*—Ronald W. Griffin
*Attorney, Agent, or Firm*—Browdy and Neimark

[57] ABSTRACT

Novel alpha-glycosylated soybean glycosides wherein one or more glucosyl residues are bound to the soybean glycoside moiety are prepared. Alpha-glycosylation can be enzymatically achieved by subjecting an aqueous solution containing a soybean glycoside, e.g. soyasaponin or isoflavonoid, and an alpha-glucosyl saccharide to an alpha-glucosyl transferase. Suitable alpha-glucosyl saccharides are liquefied starch, partially hydrolyzed starch and sucrose. Alpha-glucosidase, alpha-amylase, cyclodextrin glucanotransferase, dextransucrase, dextran dextrinase and amylosucrase are usable as the alpha-glucosyl transferase. Since in the alpha-glycosylated soybean glycosides the undesirable bitter, astringent, harsh and lingering choky tastes which are common in intact soybean glycosides are reduced or even eliminated by the alpha-glycosylation, they are suitable for use in food products or orally-usable products wherein taste is an important factor.

33 Claims, 1 Drawing Figure

FOOD PRODUCTS AND PROCESS FOR PRODUCING SAME

FIELD OF THE INVENTION

The present invention relates to food products and process for producing same. More particularly, it relates to food products containing a novel alpha-glycosyl derivative of soybean glycoside wherein one or more glucosyl residues are bound to the glycoside moiety in alpha-fashion, and a process for producing the food products.

BACKGROUND OF THE INVENTION

Soybean is used in a great quantity as an industrial material for soybean oil, defatted soybean and soybean protein. In addition, an enormous quantity of soybean has been used since ancient times as a material for cooked bean, "KINAKO"—a baked soybean four, fermented soybean, "MISO"—a soybean paste, soy sauce, soybean milk, soybean curd, dried soybean curd, "KOYA-TOFU", "ABURAGE", or "HIRYOZU".

Soybean is a very suitable material for health foods because it contains, in addition to substantial amounts of vitamin E and lecithin, large amounts of protein and fat which are riched sources for essential amino acids or fatty acids.

It is well documented that soybean contains biologically-active glycosides. For example, as reported in Chem. Pharm. Bull., Vol. 24, No. 1, pp. 121-129 (1976), or Up-to-Date Foodprocessing, Vol. 17, No. 9, pp. 39-47 (1982), soybean contains a substantial amount of soyasaponin bearing a soyasapogenol moiety as aglycon. Furthermore, as described in Up-to-Date Foodprocessing, Vol. 16, No. 5, pp. 36-40 (1981) or ibid., Vol. 17, No. 7, pp. 30-42 (1982), it has been well documented that soyasaponin exhibits biological activities, such as hypolipidemic and hypocholesterolemic effects. Also, as reported in Chem. Pharm. Bull., Vol. 24, No. 1, pp. 121-129 (1976), Up-to-Date Foodprocessing, Vol. 17, No. 7, pp. 30-42 (1982), or ibid., Vol. 17, No. 9, pp. 39-47 (1982), soybean contains substantial amounts of isoflavonoids, such as genistin, acetylgenistin, daidzin, acetyldaidzin, and glycitein 7-O-beta-glucoside. Furthermore, as described in Up-to-Date Foodprocessing, Vol. 17, No. 7, pp. 30-42 (1982), it has been well documented that isoflavonoids exhibit biological activities, such as hypolipidemic, hypocholesterolemic and antihaemolytic activities.

Accordingly, ingestion of soybean foods facilitates the uptakes of soybean glycosides, such as soyasaponin or isoflavonoid, as well as uptakes of the above described essential amino acids, essential lipids, vitamin E and lecithin. Thus, it is clear that soybean foods are much superior other health foods.

Recently, food products wherein such soybean glycosides are incorporated or soybean foods containing the same are available as dietary foods and drinks, or foods and drinks directed for promoting or retaining beauty or health. It is known that these food products, however, have a disadvantage of causing, in addition to bitter, astringent and harsh tastes, a lingering choky taste, for which the soybean glycosides are responsible.

SUMMARY OF THE INVENTION

Figure 1:
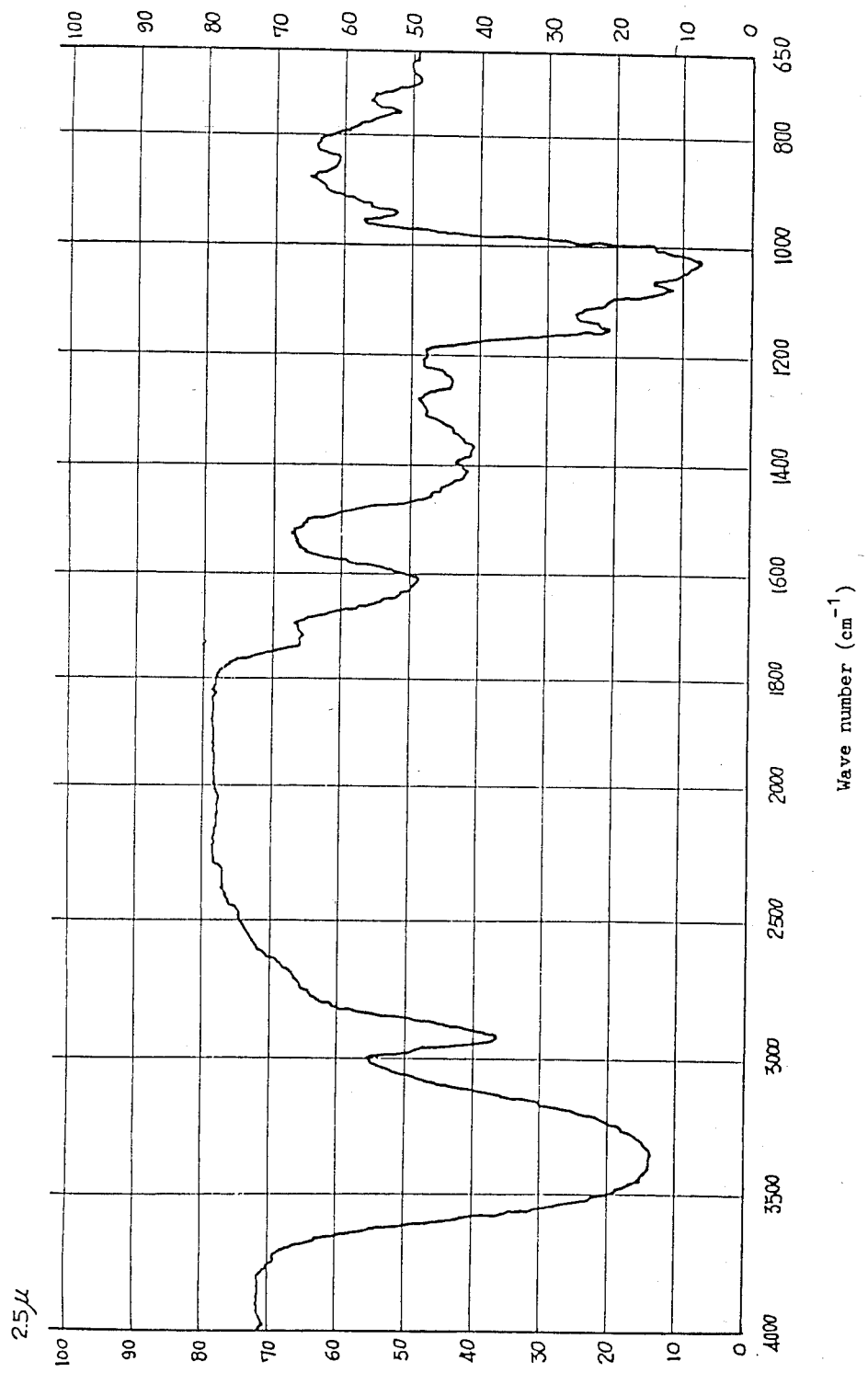
FIG. 1 shows the infrared spectrum of Sample No. 5 obtained in EXPERIMENT 3.

The present inventors have diligently investigated means to eliminate undesirable bitter, astringent, harsh and choky tastes of the soybean glycosides.

As a result, we discovered that these undesirable tastes can be substantially eliminated by converting soybean glycoside into alpha-glycosyl derivative, and that the alpha-glycosyl derivative is readily hydrolyzable into soybean glycoside by an in vivo alpha-glycosidase, e.g. alpha-glucosidase. Based on these findings, we found that alpha-glycosyl soybean glycoside can be produced and used without fear for its toxicity or additional medicinal efficacy similarly as intact soybean glycoside. Thus, we established food products containing alpha-glycosyl soybean glycoside, and a process for producing such food products.

The term "food products" as used in this specification shall mean, in addition to foods and drinks in general, all orally-usable products wherein taste is an important factor, e.g. liquors; tobacco; feeds and pet foods; cosmetics, such as gargle, dentifrice and oral-refreshing agent; and drugs, such as those for internal administration and troche.

DETAILED DESCRIPTION OF THE INVENTION

As regards alpha-glycosyl soybean glycosides which may be used in the present invention, any alpha-glycosyl soybean glycoside can be used regardless of how it is produced as long as it contains an alpha-glycosyl soybean glycoside, e.g. alpha-glycosyl soyasaponin or alpha-glycosyl isoflavonoid, in which one or more alpha-glucosyl residues are bound to the soybean glycoside moiety.

A suitable process for producing alpha-glycosyl soybean glycoside on an industrial-scale involves subjecting an aqueous solution containing a soybean glycoside and an alpha-glucosyl saccharide to an alpha-glucosyl transferase, and harvesting the resultant alpha-glycosyl soybean glycoside.

As regards usable soybean glycosides, any crude and partially-purified soybean milk which contains a substantial amount of soybean glucoside, e.g. soyasaponin or isoflavonoid, and produces alpha-glycosyl soybean glycoside is equally suitable for use in the invention, as is a highly-purified soybean glycoside.

The alpha-glucosyl saccharides suitable in the invention are those which act as a substrate for an alpha-glucosyl transferase to allow the enzyme to form alpha-glycosyl soybean glycoside with soybean glycoside. Accordingly, the use of a substrate, i.e. alpha-glucosyl saccharides including partial starch hydrolysate or sucrose, which is susceptive to the transferase, is suitable to facilitate the formation of alpha-glycosyl soybean glycoside. For example, in the case of using alpha-amylase (EC 3.2.1.1), the use of a gelatinized or partially hydrolyzed starch (dextrin) having a Dextrose Equivalent (DE) of below 1 or up to about 30 is suitable. For alpha-glucosidase (EC 3.2.1.20), the use of maltose, maltotriose or maltotetraose, or a partial starch hydrolysate having a DE of 10 to 60 is suitable. For cyclodextrin glucanotransferase (EC 2.4.1.19), cyclodextrins or a gelatinized or partially hydrolyzed starch having a DE of below 1 or up to about 60 is suitable. Sucrose is suitable in a process using dextransucrase (EC 2.4.1.5).

Gelatinized or partially hydrolyzed starch which may be used in the invention is readily preparable from a starch which may be a tuberous or subterranian stem starch from potatoes or sweet potatoes; or a cereal starch from wheat or corn. Such starch can be gelatinized by heating in suspension at a temperature about its gelatinization temperature, generally, 70°–140° C. The partial starch hydrolysate can be obtained by hydrolyzing the starch to a desired DE level with the aid of acid or amylase. Of course, two or more members of the alpha-glucosyl saccharides may be used in combination.

A usable alpha-glucosyl transferase may be one which acts on an aqueous solution containing an alpha-glucosyl saccharide and soybean glycoside, and forms an alpha-glycosyl soybean glycoside without decomposing the soybean glycoside. For example, alpha-glucosidase (EC 3.2.1.20) derived from animal source, such as pig liver, plant source, such as buckwheat seed, fungal source, such as those of genus Mucor or Penicillium, or from yeast source, such as those of genus Saccharomyces; alpha-amylase (EC 3.2.1.1) derived from various microorganism, especially, a bacterium of genus Bacillus or a fungi of genus Aspergillus; cyclodextrin glucanotransferase (EC 2.4.1.19) derived from a bacterium including those of genus Bacillus or Klebsiella; dextransucrase (Ec 2.4.1.5) derived from a bacterium including those of genus Leuconostoc; dextran dextrinase (EC 2.4.1.2) derived from a bacterium including those of genus Acetobacter; amylosucrase (EC 2.4.1.4) derived from a bacterium including those of genus Neisseria, are all advantageously usable in the invention.

The above described alpha-glucosyl transferase may not be necessarily purified prior to its use, and alpha-glycosyl soybean glycoside is generally obtainable with the use of a crude enzyme, provided that the enzyme satisfies the hereinbefore described requirements.

For example, in the case of using an animal or plant enzyme, a satisfiable crude alpha-glucosyl transferase may be prepared either by salting-out an extract of a minced animal or plant tissue using ammonium sulfate, or by precipitating the extract with an organic solvent, such as alcohol or acetone, to effect separation. If necessary, the obtained crude enzyme may be further purified in a suitable manner prior to its use.

In the production of the desired enzyme from a microorganism, a process using a solid culture, such as wheat bran culture, or a liquid culture, such as those using a fermenter, is generally carried out. Preparation of an alpha-glucosyl transferase using solid culture may be carried out by extracting the enzyme from the culture similarly as in the case of animal or plant enzyme, and the resultant crude enzyme may be, if necessary, purified in usual way prior to its use. In the case of using an alpha-glucosyl transferase obtained by a liquid culture, the culture broth can be used intact in the practice of the present invention, but an supernatant containing the desired enzyme but free of insoluble substances is generally used. An alpha-glucosyl transferase in the whole cell may be used intact, or after extraction therefrom, if necessary. Of course, a much more purified or commercially-available alpha-glucosyl transferase may be used in the invention. Furthermore, the enzymatic reaction by alpha-glucosyl transferase can be effected continuously or batch-wise by use of an immobilized alpha-glucosyl transferase. Also, alpha-glycosyl soybean glycoside may be obtained by culturing a microorganism or tissue, such as that of animal or plant, on a culture medium containing an alpha-glucosyl saccharide and soybean glycoside.

Suitable reaction conditions are those under which the alpha-glucosyl transferase acts on an aqueous solution containing a soybean glycoside and alpha-glucosyl saccharide. Generally, the soybean glycoside and alpha-glucosyl saccharide are dissolved together in water to give respective concentrations of about 0.01–30 w/w % and about 1–50 w/w %, and also to give a preferred weight ratio of alpha-glucosyl saccharide to the soybean glycoside of about 0.5–500. As regards the reaction pH and temperature for the enzymatic reaction, any pH and temperature can be employed as long as the alpha-glucosyl transferase acts on the given substrates to form alpha-glycosyl soybean glycoside. Generally, a pH in the range of 3–10 and a temperature in the range of 20°–80° C. are suitable.

Dependent upon the varieties of food products, the resultant reaction mixture containing alpha-glycosyl soybean glycoside may be used as a food product intact, or, if necessary, purified prior to its use. For example, after heat-inactivation of the enzyme and filtration, the resultant filtrate may be allowed to contact with a magnesia adsorbent, e.g. "Neucillin", "Neucillin A" or "Columnlite", products of Fuji Chemical Industry incorporation, Ltd., Toyama-ken, Japan, "Tomix Granular" or "Tomix-S Granular", "Neoalumin" or "Neoalumin S", products of Tomita Phamaceutical Co., Ltd., Narutoshi, Tokushima-ken, Japan, "M-511", a product of Hokkaido Soda Co., Ltd., Tokyo, Japan, both to adsorb and to remove coloring impurities. Thereafter, the resultant non-adsorbed liquid is harvested. The liquid may be concentrated into syrup, or, further, dried or pulverized into powder, prior to its use in food product.

If a much higher purification is desirable, alpha-glycosyl soybean glycoside and impurities may be separated according to their differences in adsorbability by use of a synthetic macroreticular resin, e.g. "Diaion HP-10", "Diaion HP-20" or "Diaion HP-40", products of Mitsubishi Chemical Industries Ltd., Tanashi, Tokyo, Japan, "Amberlite XAD-1", "Amberlite XAD-4", "Amberlite XAD-7" or "Amberlite XAD-8", products of Rohm & Haas Company, Philadelphia, Pa., USA, or "Imac Syn-42", "Imac Syn-44" or "Imac Syn-46", products of Industrie de Maatshappily Activate N.V., Amsterdam, Netherland. For example, if separation of free saccharides from soybean glycoside compounds, including alpha-glycosyl soybean glycoside and residual soybean glycoside, is desirable, the reaction mixture is first applied on any one of the above described magnesia adsorbents to remove coloring impurities, then further on a column of a synthetic macroreticular resin, whereby the compounds are adsorbed thereon while the saccharide is eluted. Thereafter, the adsorbed soybean glycoside compounds are eluted with a low alcohol solution, e.g. 40 v/v % aqueous ethanol solution, and concentrated into a syrup which may be dried and pulverized to harvest a powder, prior to its use in a food product.

Furthermore, by applying a solution containing alpha-glycosyl soybean glycoside and residual soybean glycoside on a column of a synthetic macroreticular resin to allow soybean glycoside to selectively adsorb thereon, an alpha-glycosyl soybean glycoside preparation having a much higher purity can be harvested from the non-adsorbed part. Such preparation may be, if necessary, further purified and deionized with an ion exchange resin, e.g. strongly-acidic ion exchange resin (OH-form) or weakly-anionic ion exchange resin (H- form), or chromatographed to harvest the desired fraction, prior to its use.

Since, unlike intact soybean glycoside, the alpha-glycosyl soybean glycoside obtained in this manner is almost free from the undesirable tastes, i.e. bitter, astringent, harsh or choky taste, it may be usable alone as a food product, or in combination with other ingredient(s), regardless of its purification degree or purity.

Furthermore, since alpha-glycosyl soybean glycoside is easily hydrolyzable into soybean glycoside by in vivo alpha-glycosidase, such as alpha-glucosidase, it can be used freely without fear for its toxicity or additional medicinal efficacy similarly as intact soybean glycoside in uses wherein the inherent medicinal efficacies of soybean glycoside, e.g. hypolipidemic, hypocholesterolemic, a peptic, intestine-regulating, anti-inflammatory or expectorant effect, is expected. Accordingly, a food product containing alpha-glycosyl soybean glycoside is advantageously usable as a food product directed to improvement, maintenance or restoration of health. Thus, in addition to food products in general, e.g. seasoning, confectioneries, frozen desserts, syrups, processed fruits or vegetables, pickles or pickled products, processed meats or fish meat, delicacies, canned or bottled foods, liquors, soft drinks, or convenient foods or mixes, the concept "food products" according to the invention shall be extended to various orally-usable products in liquid, paste or solid form, such as feeds and pet foods for domestic animal or fowl, or fish, tobaccos, cosmetics and drugs including dentifrice, lipstick, lipcream, medicine for internal administration, troche, cod liver oil drop, oral refreshing agent or gargle, as long as taste is an important factor thereof. The medicinal efficacy of alpha-glycosyl soybean glycoside in these food products may be enhanced by incorporating thereto one or more substances, e.g. crude drugs or medicines for promoting nutrition.

As regards the procedure by which alpha-glycosyl soybean glycoside is prepared into, or added to such food products, any conventional procedure can be employed in the invention as long as the food products can be prepared with, or added with alpha-glycosyl soybean glycoside before completion of their processing; for example, by mixing, kneading, dissolving, soaking, permeating, spraying, coating and injection.

The alpha-glycosyl soybean glycoside according to the invention will be explained hereinafter with reference to some experiments.

EXPERIMENT 1

Preparation of alpha-glycosyl soybean glycoside

EXPERIMENT 1—1

Preparation of alpha-glucosyl transferase

A seed culture of *Bacillus stearothermophilus* FERM-P No. 2222 was inoculated on 10 liters of a sterilized liquid medium, consisting of 2 w/v % soluble starch, 1 w/v % NH$_4$NO$_3$, 0.1 w/v % KH$_2$PO$_4$, 0.05 w/v % MgSO$_4$.7H$_2$O, 0.5 w/v % corn steep liquor, 1 w/v % CaCO$_3$ and water, and cultured thereon at 50° C. for 3 days under aeration-agitation conditions. After completion of the culture, the culture broth was centrifuged, and the supernatant was added with ammonium sulfate to give a 0.7 saturation and also to effect salting-out to obtain a crude enzyme preparation having about 80,000 units of cyclodextrin glucanotransferase (EC 2.4.1.19).

One unit of cyclodextrin glucanotransferase activity is defined as the amount of enzyme that effects complete disappearance of the iodine development of 15 mg soluble starch under the following conditions: To 5 ml of a 0.3 w/w % soluble starch solution in 0.02M acetate buffer (pH 5.5.), containing $2\times10^{-3}$M calcium chloride, is added 0.2 ml of a dilute enzyme solution, and the mixture is incubated at 40° C. for 10 minutes. Thereafter, 0.5 ml of the reaction mixture is added to 15 ml of 0.02N sulfuric acid to suspend the enzymatic reaction, and the mixture is admixed with 0.2 ml of 0.1N I$_2$-KI solution to effect iodine development. Then, the absorbance of the admixture is determined at a wave length of 660 nm.

EXPERIMENT 1—2

Preparation of soybean glycosides

Four kg of defatted soybean was added with 10 liters of methanol, and subjected to extraction at 60° C. for 3 hours, followed by filtration. The resultant residue was subjected twice to additional extractions using methanol similarly as above. All of the extracts were pooled, concentrated in vacuo to evaporate methanol, and dried to obtain a solid. An aqueous solution of about 10 w/w % of the solid was filtered, and applied on a column, packed with 5 liters of "HP-20", trade name of a commercial synthetic macroreticular resin, a product of Mitsubishi Chemical Industries Ltd., Tokyo, Japan. The column was sufficiently washed with water to remove coloring impurities, and then charged with 15 liters of methanol. The obtained eluate was concentrated in vacuo to evaporate methanol, and then dried and pulverized. The obtained powder was dissolved in 3 liters of methanol, and then added with 27 liters of ethyl ether. After 1-day standing and filtration, the filtrate was concentrated in vacuo at below 60° C., and pulverized to obtain about 25 g of isoflavonoid powder. Also, the remaining precipitate was concentrated in vacuo at below 60° C., and pulverized to obtain about 20 g of soyasaponin powder.

EXPERIMENT 1—3

Enzymatic reaction

Ten g of soyasaponin or isoflavonoid, prepared by the method as disclosed in EXPERIMENT 1—2, and 50 g of maltodextrin (DE 20) were dissolved together in 100 ml of hot water. After adjusting pH to 6.0, the resultant solutions were added with 500 units of a crude cyclodextrin glucanotransferase preparation, prepared by the method as disclosed in EXPERIMENT 1—1, and incubated at pH 6.0 and 60° C. for 24 hours to effect enzymatic reaction. After being kept at 95° C. for 15 minutes to heat-inactivate the enzyme, the reaction mixtures, Sample No. 3 in Table I and Sample No. 8 in Table II, were filtered, concentrated in vacuo below 60° C., and dried to obtain powders, Sample No. 4 in Table I and Sample No. 9 in Table II.

Samples No. 1 and No. 2 in Table I and Samples No. 6 and No. 7 in Table II, the controls, were prepared similarly as above by dissolving 10 g of soyasaponin or isoflavonoid together with or without 50 g maltodextrin in 100 ml of hot water while heating, and incubating the resultant mixtures in the absence or presence of thermally-preinactivated 500 units of the cyclodextrin glucanotransferase.

The formulations of the Samples No. 1–4 and No. 6–9 are given in Tables I and II respectively.

TABLE I

|  | Sample No. 1* | Sample No. 2* | Sample No. 3** | Sample No. 4** |
| --- | --- | --- | --- | --- |
| Formulation | Soyasaponin 10 g | Soyasaponin 10 g + Maltodextrin 50 g + Thermally-preinactivated 500 units of the enzyme | Soyasaponin 10 g + Maltodextrin 50 g + Active 500 units of the enzyme | Soyasaponin 10 g + Maltodextrin 50 g + Active 500 units of the enzyme |

Note:
*control; and **present invention.

TABLE II

|  | Sample No. 6* | Sample No. 7* | Sample No. 8** | Sample No. 9** |
| --- | --- | --- | --- | --- |
| Formulation | Isoflavonoid 10 g | Isoflavonoid 10 g + Maltodextrin 50 g + Thermally-preinactivated 500 units of the enzyme | Isoflavonoid 10 g + Maltodextrin 50 g + Active 500 units of the enzyme | Isoflavonoid 10 g + Maltodextrin 50 g + Active 500 units of the enzyme |

Note:
*control; and **present invention.

EXPERIMENT 2

Comparison test

An aqueous solution was prepared by dissolving Sample No. 4 in water to give the same concentration of Sample No. 3. Thereafter, an organoleptic test using aqueous solutions of Samples No. 1 through No. 4 was carried out at 25° C. with 20 panel members, and the panel was asked to choose the most desirable and the most undesirable preparations along with comments on their taste qualities. The results are given in Table III.

A similar organoleptic test was carried out on Samples No. 6 through No. 10.

The results are given in Table IV.

As is apparent from Table III and IV, the superiorities of Samples No. 3 and No. 4 over Samples No. 1 and No. 2 and of Samples No. 8 and No. 9 over Samples No. 6 and No. 7 in taste qualities are obvious. Since the present alpha-glycosyl soybean glycosides were found free of the undesirable tastes which are common in conventional soybean glycosides and of their saccharide mixtures, it can be intaken intact.

EXPERIMENT 3

Identification of alpha-glycosyl soybean glycosides

EXPERIMENT 3—1

Identification of alpha-glycosyl soyasaponin

Fifty g of a sample, prepared similarly as Sample No. 4 in EXPERIMENT 1—3, was dissolved in 100 ml of water, and the resultant aqueous solution was added with 2 g of "M-511", trade name of a commercial magnesia adsorbent, a product of Hokkaido Soda Co., Ltd., Tokyo, Japan. The mixture was subjected to 30-minute standing under gentle stirring conditions, followed by filtration. The filtrate was applied on a column, packed with 200 ml of "Diaion HP-20", trade name of a commercial synthetic macroreticular resin, a product of Mitsubishi Chemical Industries, Incorporation, Tokyo, Japan, and the column was washed with water in an amount sufficient to remove free saccharides. Then, 2 liters of a 50 v/v % aqueous methanol solution was charged to the column to elute the soyasaponin compounds including alpha-glycosyl soyasaponin, and the

TABLE III

| Judgement | Sample No. 1* | Sample No. 2* | Sample No. 3** | Sample No. 4** |
| --- | --- | --- | --- | --- |
| Most desirable | 0 | 0 | 10 | 10 |
| Most undesirable | 11 | 9 | 0 | 0 |
| Taste quality | Strongly bitter and harsh. Choky taste lingers to give an undesirable after-taste. | | Almost free of bitter and harsh tastes, as well as of choky taste. | |

Note:
*control; and **present invention

TABLE IV

| Judgement | Sample No. 6* | Sample No. 7* | Sample No. 8** | Sample No. 9** |
| --- | --- | --- | --- | --- |
| Most desirable | 0 | 0 | 10 | 10 |
| Most undesirable | 11 | 9 | 0 | 0 |
| Taste quality | Strongly bitter and astringent. Choky taste lingers to give an undesirable after-taste. | | Almost free of bitter and astringent tastes, as well as of choky taste. | |

Note:
*control; and **present invention eluate was concentrated, dried, and pulverized to obtain about 9 g of powder, Sample No. 5.

Sample No. 5 is an odorless, readily water-soluble and almost neutral substance in pale-yellow powder form almost free from bitter, harsh or lingering choky taste. This Sample is partially soluble in a low alcohol, such as methanol, ethanol or n-butanol, but hardly in chloroform or ethyl ether. An infrared spectrum of Sample No. 5 obtained according to the KBr tablet method is given in FIG. 1.

A small amount of Sample No. 5 dissolved in a minimum amount of water was subjected to a commercial crystalline glucoamylase (EC 3.2.1.3) at 50° C. in 0.02M acetate buffer (pH 5.0) to effect enzymatic reaction. In the course of the reaction, small amounts of the reaction mixture were periodically sampled, and spotted on "Kieselgel 60", trade name of a commercial thin-layer plate, a product of Merck & Co., Inc., Rahway, N.J., USA, followed by ascending development using a solvent mixture of chloroform, methanol and water (65:35:10). After drying, the thin-layer plate was sprayed with 1% Ce(SO$_4$)$_2$ solution in 10% sulfuric acid, and allowed to develop at 100° C. for 10 minutes under heat-drying conditions. D-Glucose and a soyasaponin, prepared by the method as described in EXPERIMENT 1—2, both used as the controls, were spotted and developed on the same thin-layer plate.

As a result, while a series of large deep redish purple spots and redish purple spots relatively small in size were found in the chromatogram of the soyasaponin at $R_f$ 0.26, 0.31 and 0.34, and $R_f$ 0.20, 0.38 and 0.41 respectively, several newly-formed redish purple spots relatively small in size, and a redish purple tailing were found in the chromatogram of Sample No. 5 at $R_f$ from near 0.17 to 0.10, and around origin respectively, in addition to six relatively small soyasaponin spots.

Accordingly, it can be concluded that Sample No. 5 is a mixture of a small amount of residual soyasaponin and a series of novel substances corresponding to the spots and tailing at $R_f$ from near 0.17 to origin which are formed by the alpha-glucosyl transferase.

Sample No. 5 was subjected to glucoamylase, and the reaction mixture was periodically sampled and chromatographed similarly as above. As a result, the series of novel substances corresponding to the newly-formed tailing were found to be gradually hydrolyzed in the course of the reaction, and to finally give redish purple soyasaponin spots and a brown D-glucose spot at $R_f$ near 0.18.

Separately, Sample No. 5 was subjected to a partially-purified alpha-glucosidase from a pig liver extract, and the reaction mixture was chromatographed. As a result, it was confirmed that the novel substances in Sample No. 5 are easily hydrolyzable by the enzyme into soyasaponin and D-glucose, as was in the case of using glucoamylase.

Based on these experimental results, it can be concluded that the novel substances, formed by alpha-glucosyl transferase, are substances wherein one or more D-glucose residues are bound to soyasaponin moiety in alpha-fashion. This suggests that alpha-glycosyl soyasaponin is easily hydrolyzable in vivo into soyasaponin and D-glucose when ingested.

A sample, prepared similarly as Sample No. 5, was chromatographed on a silica gel column using a developing solvent of chloroform, methanol and water (65:35:10), and a fraction from $R_f$ near 0.17 to origin, containing the novel substances, was recovered, and dried into powder. This powder is of a readily water-soluble, neutral substance free from bitter and harsh tastes, as well as from lingering choky taste. The substance is partially soluble in a low alcohol, such as methanol, ethanol or n-butanol, but insoluble in chloroform or ethyl ether.

Also, unlike intact soyasaponin but similarly as Samples No. 3 and No. 4, Sample No. 5 was almost free from bitter, harsh and lingering choky tastes.

EXPERIMENT 3—2

Identification of alpha-glycosyl isoflavonoid

Fifty g of a sample, prepared similarly as Sample No. 9 in EXPERIMENT 1—3, was dissolved in 100 ml of water, and the resultant aqueous solution was added with 2 g of "M-511", trade name of a commercial magnesia adsorbent, a product of Hokkaido Soda Co., Ltd., Tokyo, Japan. The mixture was subjected to 30-minute standing under gentle stirring conditions, followed by filtration. The filtrate was applied on a column, packed with 200 ml of "Diaion HP-20", trade name of a commercial synthetic macroreticular resin, a product of Mitsubishi Chemical Industries, Incorporation, Tokyo, Japan, and the column was washed with water in an amount sufficient to remove free saccharides. Then, 2 liters of a 50 v/v % aqueous methanol solution was charged to the column to elute the isoflavonoid compounds including alpha-glycosyl isoflavonoid, and the eluate was concentrated, dried, and pulverized to obtain about 8 g of powder, Sample No. 10.

Sample No. 10 is an odorless, readily water-soluble and almost neutral substance in pale-yellow powder form almost free from bitter, astringent or lingering choky taste. This Sample is partially soluble in a low alcohol, such as methanol, ethanol or n-butanol, but hardly in chloroform or ethyl ether.

A small amount of Sample No. 10 dissolved in a minimum amount of water was subjected to a commercial crystalline glucoamylase (EC 3.2.1.3) at 50° C. in 0.02M acetate buffer (pH 5.0) to effect enzymatic reaction. In the course of the reaction, small amounts of the reaction mixture were periodically sampled, and spotted on "Kieselgel 60", trade name of a commercial thin-layer plate, a product of Merck & Co., Inc., Rahway, N.J., USA, followed by ascending development using a solvent mixture of chloroform, methanol and water (65:35:10). After drying, the thin-layer plate was irradiated with uv-light to observe fluorescent spots. Thereafter, the thin-layer plate was sprayed with 1% Ce(SO$_4$)$_2$ solution in 10% sulfuric acid, and allowed to develop at 100° C. for 10 minutes under heat-drying conditions. D-Glucose and an isoflavonoid, prepared by the method as described in EXPERIMENT 1—2, both used as the controls, were spotted and developed on the same thin-layer plate.

As a result, isoflavonoid gave a strong fluorescent spot, and developed into brown or yellow brown by the developing agent. While a series of large deep red spots and relatively small spots were found in the chromatogram of the isoflavonoid at $R_f$ 0.97, 0.93, 0.79 and 0.75 and $R_f$ 0.88 and 0.90 respectively, several newly-formed relatively small spots, and a tailing were found in the chromatogram of Sample No. 10 at $R_f$ 0.58, 0.53, 0.39 and 0.36, and $R_f$ from near 0.26 to near origin respectively, in addition to six relatively small isoflavonoid spots.

Accordingly, it can be concluded that Sample No. 10 is a mixture of a small amount of residual isoflavonoid and a series of novel substances corresponding to the spots at $R_f$ 0.58, 0.53, 0.39 and 0.36, and a tailing from $R_f$ near 0.26 to origin which are formed by the alpha-glucosyl transferase.

Sample No. 10 was subjected to glucoamylase, and the reaction mixture was periodically sampled and chromatographed similarly as above. As a result, the series of novel substances corresponding to the newly-formed tailing were found to be gradually hydrolyzed in the course of the reaction, and to finally give redish purple isoflavonoid spots and a brown D-glucose spot at $R_f$ near 0.18.

Separately, Sample No. 10 was subjected to a partially-purified alpha-glucosidase from a pig liver extract, and the reaction mixture was chromatographed. As a result, it was confirmed that the novel substances in Sample No. 10 are easily hydrolyzable by the enzyme into isoflavonoid and D-glucose, as was in the case of using glucoamylase.

Based on these experimental results, it can be concluded that the novel substances, formed by alpha-glycosyl transferase, are substances wherein one or more D-glucose residues are bound to isoflavonoid moiety in alpha-fashion. This suggests that alpha-glycosyl isoflavonoid is easily hydrolyzable in vivo into isoflavonoid and D-glucose when ingested.

A sample, prepared similarly as Sample No. 10, was chromatographed on a silica gel column using a developing solvent of chloroform, methanol and water (65:35:10), and a fraction from $R_f$ near 0.58 to origin, containing the novel substances, was recovered, and dried into powder. This powder is of a readily water-soluble, neutral substance free from bitter and astringent tastes, as well as from lingering choky taste. The substance is partially soluble in a low alcohol, such as methanol, ethanol or n-butanol, but insoluble in chloroform or ethyl ether.

Also, unlike intact isoflavonoid but similarly as Samples No. 8 and No. 9, Sample No. 10 is almost free from bitter, astringent and lingering choky tastes.

Accordingly, it can be also concluded that removal or elimination of the undesirable tastes, i.e. bitter, astringent and lingering choky tastes, from a soybean glycoside, which is one of the objects of the present invention, is attainable by subjecting an aqueous solution containing the soybean glycoside and an alpha-glucosyl saccharide to an alpha-glucosyl transferase thereby to form alpha-glycosyl soybean glycoside.

The present invention is further illustrated by the following EXAMPLEs.

EXAMPLE 1

Syrup containing alpha-glycosyl soyasaponin

A seed culture of *Mucor javanicus* IFO 4570 as inoculated on 5 liters of a sterilized culture medium, consisting of 4 w/v % maltose, 0.1 w/v % KH$_2$PO$_4$, 0.1 w/v % NH$_4$NO$_3$, 0.1 w/v % NaNO$_3$, 0.05 w/v % MgSO$_4$.7-H$_2$O, 0.05 w/v % KCl, 0.2 w/v % polypeptone, water, and 1 w/v % CaCO$_3$ (separately sterilized and added), and cultured thereon at 30° C. for 44 hours under aeration-agitation conditions. Four hundred and eighty g of the wet cells, obtained from the culture broth, was added with 5 liters of 4M urea solution in 0.5M acetate buffer (pH 5.3), and allowed to stand at 30° C. for 40 hours. Then, the supernatant was dialyzed against running tap water overnight, added with ammonium sulfate to bring 0.9 saturation, and allowed to stand at 4° C. overnight. After centrifugation, the resultant precipitate was suspended in 100 ml of acetate buffer (pH 6.0), and centrifuged to obtain a supernatant which was usable as a solution of alpha-glucosidase (EC 3.2.1.20).

Thirty g of soyasaponin, prepared by the method as described in EXPERIMENT 1—2, and 300 g of maltodextrin (DE 40) were dissolved together in 500 ml of a hot water, and the resultant solution was adjusted to 50° C. and pH 6.0, added with the alpha-glucosidase solution, and incubated for 24 hours to effect enzymatic reaction.

After inactivating the enzyme by heating, the reaction mixture was filtered, and the resultant filtrate was applied first on a column, packed with 5 g of "Columnlite", trade name of a commercial magnesia adsorbent, a product of Fuji Chemical Industries Incorporation, Ltd., Toyama-ken, Japan, to remove coloring impurities, then on a column on ion exchange resins, "Amberlite IR-120 B (H-form)" and "Amberlite IRA-94 (OH-form)" to effect deionization, followed by in vacuo concentration to obtain a syrup containing alpha-glycosyl soyasaponin having a moisture content of 20%. The overall yield was about 95% on the basis of dry solid.

This syrup is almost free from undesirable tastes, such as bitter, harsh or lingering choky taste, but is somewhat mildly sweet. Thus, it may be ingested intact, or used in a food product.

EXAMPLE 2

Powder containing alpha-glycosyl soyasaponin

A seed culture of *Bacillus magaterium* FERM-P No. 935 was inoculated on 5 liters of a fresh culture medium having the same composition as used in EXPERIMENT 1—1, and cultured thereon at 28° C. for 3 days under aeration-agitation conditions. After completion of the cultivation, the culture broth was centrifuged to obtain a supernatant which was then added with ammonium sulfate to give 0.7 saturation, followed by an additional centrifugation to harvest a precipitate containing $3 \times 10^5$ units of cyclodextrin glucanotransferase activity as defined in EXPERIMENT 1—1.

Sixty g of soyasaponin, prepared by the method as described in EXPERIMENT 1—2, and 180 g of beta-cyclodextrin were dissolved together in 500 ml of water while heating, and the resultant solution was cooled to 50° C., adjusted to pH 5.5, added with 15 units of the cyclodextrin glucanotransferase per g beta-cyclodextrin, and incubated at 50° C. and pH 5.5 for 24 hours to effect enzymatic reaction. After inactivating the enzyme by heating, the reaction mixture was filtered, and the filtrate was applied on a column, packed with 3 liters of "Amberlite XAD-7", trade name of a commercial macroreticular resin, a product of Rohm & Haas company, Philadelphia, Pa., USA. The column was first washed with sufficient water to remove free saccharides, thereafter charged with 10 liters of 50 v/v % aqueous ethanol solution. The eluate was concentrated, and dried to obtain about 75 g of powder containing alpha-glycosyl soyasaponin.

The powder was chromatographed using a thin-layer plate similarly as Sample No. 5 in EXPERIMENT 3. As a result, several redish purple spots and a slight tailing were noted in the chromatogram at $R_f$ near 0.17–0.10 and down to origin, in addition to the soyasaponin spots.

The powder containing alpha-glycosyl soyasaponin is almost free from undesirable tastes, such as bitter, harsh or lingering choky taste. Thus, it may be ingested intact, or, if necessary, seasoned with sweetening or souring agent prior to its use.

Separately, the powder was first subjected to glucoamylase, then chromatographed, similarly as Sample No. 5 in EXPERIMENT 3. As a result, it was confirmed that, during the enzymatic reaction, the novel substances from $R_f$ near 0.17 to origin gradually hydrolyze to give a series of redish purple spots at $R_f$ 0.20, 0.26, 0.31, 0.34, 0.38 and 0.41, and a brown spot at $R_f$ 0.18, which correspond to soyasaponin and D-glycose respectively.

EXAMPLE 3

Syrup containing alpha-glycosyl soyasaponin

Ten kg of defatted soybean was added with 25 liters of methanol, and allowed to stand at 50° C. for 3 hours to effect extraction, followed by filtration. The resultant residue was subjected twice to additional extractions using methanol similarly as above. The obtained three extracts were pooled, and concentrated in vacuo to evaporate methanol, and dried to obtain a solid. An aqueous solution of 10 w/w % of the solid was filtered, and applied on a column, packed with 8 liters of "HP-10", trade name of a commercial synthetic macroreticular resin, a product of Mitsubishi Chemical Industries Ltd., Tokyo, Japan, which was then sufficiently washed to remove impurities. Thereafter, to the column was charged 20 liters of methanol, and the eluate was concentrated in vacuo to evaporate methanol, dried, and pulverized to obtain about 120 g of powder containing soyasaponin.

Fifty g of the powder and 300 g of maltodextrin (DE 30) were dissolved together in 300 ml of water, and then added with 10 units of a cyclodextrin glucanotransferase per g maltodextrin, prepared by the method as described in EXPERIMENT 1—1. The mixture was incubated at pH 5.5 and 60° C. for 24 hours to effect enzymatic reaction. After inactivating the enzyme by heating, the reaction mixture was filtered, and the filtrate was concentrated to obtain a syrup containing alpha-glycosyl soyasaponin having a moisture content of 20%. The overall yield was about 97% on the basis of dry solid.

This syrup is almost free from undesirable tastes, such as bitter, harsh or choky taste, but is somewhat mildly sweet. Thus, the syrup may be ingested intact, or used in various types of food products.

EXAMPLE 4

Syrup containing alpha-glycosyl soyasaponin

One kg of a defatted soybean was added with 10 liters of water, and kept at 50° C. for 1 hour under gentle stirring conditions, followed by filtration. The resultant filtrate was added with lactic acid to bring its pH to 4.5, kept at 85° C. for 10 minutes, and centrifuged to obtain a supernatant (soybean whey).

The supernatant was neutralized with an aqueous caustic soda solution, added with 50 g of sucrose, 2 g of yeast extract, 8 g of $KH_2PO_4$ and 24 g of $K_2HPO_4$, kept at 100° C. for 15 minutes to effect sterilization, and cooled to prepare a cultuure medium. A 1% seed culture of *Leuconostoc mesenteroides* IAM 1151 was inoculated thereto, and cultured thereon at 25° C. for 24 hours. After centrifuging the culture broth, the supernatant was added with 10 g of "M-511", trade name of a commercial magnesia adsorbent, product of Hokkaido Soda Company, Ltd., Tokyo, Japan, allowed to stand for 15 minutes under gentle stirring conditions, and filtered to remove coloring impurities. Then, the filtrate was deionized by applying to ion exchange resins, "Amberlite IR-200 C (H-form)" and "Amberlite IRA-93 (OH-form)", and concentrated in vacuo to obtain about 60 g of syrup containing alpha-glycosyl soyasaponin having a moisture content of 30%.

The alpha-glycosyl soyasaponin component in this syrup was gradually hydrolyzed by isomaltodextranse (EC 3.2.1.94) into soyasaponin and isomaltose. This confirms that one or more D-glucose residues are bound to soyasaponin moiety in alpha-1,6 fashion in the alpha-glycosyl soyasaponin molecule.

This syrup is almost free from undesirable tastes, such as bitter, harsh or choky taste. Thus, it may be ingested intact, or used in various types of food products.

EXAMPLE 5

Syrup containing alpha-glycosyl soyasaponin

To 1 liter of water was added 300 g of potato starch, and 60 g of a powder containing soyasaponin, prepared by the method as described in EXAMPLE 3, and the resultant suspension was adjusted to pH 6.0, added with a commercial saccharifying alpha-amylase (EC 3.2.1.1) of a bacterium origin, a product of Seikagaku Kogyo Co., Ltd., Tokyo, Japan, in an amount of 10 units per g starch in terms of the enzyme unit as defined in EXPERIMENT 1—1, and liquefied by heating to 80° C. under stirring conditions. After completion of the liquefaction, the resultant was cooled to 60° C., and subjected to further enzymatic reaction for an additional 2 days. Similarly as in EXAMPLE 1, the reaction mixture was heated to inactivate the alpha-amylase, filtered, purified with a magnesia adsorbent and ion exchange resins, concentrated in vacuo, dried, and pulverized to obtain a powder containing alpha-glycosyl soyasaponin. The overall yield was about 96% on the basis of dry solid.

This powder is almost free from undesirable tastes, such as a bitter, harsh or choky taste, but is somewhat mildly sweet. Thus, it may be ingested intact, or used in a food product.

EXAMPLE 6

Sweetener

One kg of "FUNMATSU MABIT®", trade name of a commercial crystalline maltitol powder, available from Hayashibara Shoji, Inc., Okayama, Japan, was admixed with 30 g of "α-G-Sweet", trade name of a commercial alpha-glycosyl stevioside, a product of Toyo Sugar Refining Co., Ltd., Tokyo, Japan, and 20 g of a syrup containing alpha-glycosyl soyasaponin, prepared by the method as described in EXAMPLE 1. The resultant admixture was placed and shaped in a mold by applying a slightly high pressure, and the content was released therefrom, and dried with a hot air to obtain a sweetener in cube, about 3 g each.

The sweetener containing alpha-glycosyl soyasaponin is suitable for sweetening coffee, tea or soft drink and for imparting thereto the inherent medicinal efficacy of soyasaponin, e.g. hypolipidemic or hypocholesterolemic effect. Also, the product is suitable as a low-cariogenic sweetener, as well as a low-caloric sweetener.

EXAMPLE 7

Sweetener

Fifty g of a powder containing alpha-glycosyl soyasaponin, prepared by the method as described in EXAMPLE 2, was dissolved in 20 ml of water. To the solution was admixed 1 kg of honey to obtain a sweetener containing alpha-glycosyl soyasaponin.

This sweetener may be ingested intact, and is suitable for sweetening a health food or drink for beauty, as well as for improving the taste quality of a herb medicine.

EXAMPLE 8

Hard candy

While heating, 6 kg of sucrose, 3 kg of "SUN-MALT®", trade name of a crystalline maltose powder, a product of Hayashibara Co., Ltd., Okayama, Japan, and 1 kg of a syrup containing alpha-glycosyl soyasaponin, prepared by the method as described in EXAMPLE 3, were dissolved in 5 liters of water, and the resultant solution was boiled up at 145°–150° C., and concentrated in vacuo to give a moisture content below 2%. The resultant concentrate was admixed with 80 g of citric acid, and small amounts of lemon flavor and coloring agent, and shaped in conventional manner to obtain the titled product.

The product is suitable as a hard candy exhibiting the inherent efficacy of soyasaponin, e.g. hypolipidemic or hypocholesterolemic effect.

EXAMPLE 9

Modified soybean milk

Ten kg of raw soybean was dehulled, autoclaved at 130° C. for 10 minutes, ground while pouring thereto about 9 volumes of hot water, and centrifuged to remove the residue—"OKARA", obtaining about 60 liters of soybean milk.

Ten kg of maltodextrin (DE 20) and 10 units of a cyclodextrin glucanotransferase, prepared by the method as described in EXPERIMENT 1—1, per g maltodextrin, were added to the soybean milk, and kept at pH 5.5–6.5 and 65° C. for 20 hours to effect enzymatic reaction. Thereafter, the reaction mixture was heated to inactivate the enzyme, and filtered to obtain a filtrate. To the filtrate was admixed 5 kg of "SUN-MALT®", trade name of a commercial crystalline maltose powder, a product of Hayashibara Co., Ltd., Okayama, Japan, 200 g of soybean oil, 50 g of common salt, and a small amount of lecithin, and the resultant admixture was sterilized with heating, deodorized in vacuo, homogenized, cooled, packed, and packaged to obtain the titled product.

Unlike conventional soybean milk of similar type, the product is a readily drinkable beverage free from bitter, harsh and choky tastes.

EXAMPLE 10

Chewing gum

After softening by heating, 2 kg of gum base was admixed with 7 kg of "FUNMATSU MABIT®", trade name of a commercial crystalline maltitol powder, available from Hayashibara Shoji, Inc., Okayama, Japan, 20 g of "α-G-Sweet", trade name of a commercial alpha-glycosyl stevioside, a product of Toyo Sugar Refining Co., Ltd., Tokyo, Japan, 300 g of a powder containing alpha-glycosyl soyasaponin, prepared by the method as described in EXAMPLE 5, and small amounts of menthol and coloring agent. The admixture was then kneaded with a roll, and shaped in conventional manner to obtain the titled product.

Since the product is excellent in texture and sweetness, it is suitable as a chewing gum exhibiting the inherent medicinal efficacy of soyasaponin, e.g. expectorant or hypocholesterolemic effect. Also, the product is suitable as a low-caloric or low-cariogenic chewing gum.

EXAMPLE 11

Chocolate

Forty kg of cacao paste, 10 kg of cacao butter, 15 kg of powdered sugar, 15 kg of whole milk powder, and 500 g of a powder containing alpha-glycosyl soyasaponin, prepared by the method as described in EXAMPLE 2, were mixed, and the mixture was placed in a refiner to reduce its particle size. Thereafter, the content was transferred into a conche, added with 500 g lecithin, and kneaded at 50° C. for 2 days therein. Then, the content was placed in a shaping apparatus, and solidified therein to obtain the titled product.

The product is excellent in texture and flavor, and free from fat- or sugar-blooming during storage. The product is suitable as a chocholate exhibiting the inherent medicinal efficacy of soyasaponin, e.g. hypolipidemic or hypocholesterolemic effect.

EXAMPLE 12

Sour milk beverage

After pasteurizing at 80° C. for 20 minutes, 10 kg of defatted milk was cooled to 40° C., added with 300 g of a starter, and fermented at 35°–37° C. for 10 hours. The resultant was homogenized, and admixed with 9.6 kg of sucrose and 400 g of a syrup containing alpha-glycosyl soyasaponin, prepared by the method as described in EXAMPLE 4, at 80°–85° C. under stirring conditions to effect pasteurization. The admixture was cooled, added with a small amount of flavor, and bottled to obtain the titled product.

The product is suitable as a sour milk beverage exhibiting the inherent medicinal efficacies of soyasaponin.

EXAMPLE 13

Carbonated beverage

In 8 liters of water was dissolved 1.97 kg of a commercial isomerized sugar solution (conversion degree 55%), 12.5 g of a syrup containing alpha-glycosyl soyasaponin, prepared by the method as described in EXAMPLE 3, 23 g of citric acid, 0.2 g of vitamin $B_1$ nitrate and 0.5 g of vitamin $B_6$ while stirring, and the resultant solution was gassed with 2 volumes of carbon dioxide with the aid of a carbonator in conventional manner to obtain the titled product.

The product is suitable as a health drink exhibiting the inherent medicinal efficacies of soyasaponin.

EXAMPLE 14

Jelly

Three hundred g of prune extract (moisture content 30%), 2 kg of sucrose, 3 kg of glucose, 2 kg of corny syrup (moisture content 25%), 16 g of a syrup containing alpha-glycosyl soyasaponin, prepared by the method described in EXAMPLE 3, and 2.13 liters of water were admixed, and the admixture was boiled to give a moisture content of 20% while heating and stirring. The resultant was added with a 60° C. aqueous solution, wherein 350 g of "Yellow Ribbon", trade name of a commercial high-methoxyl pectin, available from Yukijirushi Shokuhin KK, Tokyo, Japan, was dissolved to give a concentration of 5 w/w %, boiled until its moisture content reached 22–23% while heating, added with 200 g of 50 w/w % aqueous citric acid solution under vigorous stirring conditions, poured into a mold at a temperature above 90° C., and solidified therein by 8 hour-standing under ambient conditions. The content was removed therefrom, dried with a 40° C. air, and packaged to obtain the titled product.

The product is a jelly excellent in biting properties. The product is suitable as a jelly exhibiting the inherent medicinal efficacies of soyasaponin.

EXAMPLE 15

Jelly

One and half kg of sucrose, 30 g of sodium citrate, 110 g of "GF-100", trade name of a commercial stabilizer, product of Nitta Gelatine Co., Ltd., Osaka, Japan, 12.5 g of a syrup containing alpha-glycosyl soyasaponin, prepared by the method as described in Example 3, and 7.3 liters of water, were mixed while heating. The mixture was then kept at 80° C. for 10 minutes, and admixed with 1 kg of prune extract (moisture content 30%) and 30 g citric acid, dissolved in a minimum amount of water, while stirring. The resultant was packed in a vessel at 60°–70° C., sterilized at 90° C. for 30 minutes, and cooled to obtain the titled product.

The product is a jelly having a refreshing taste and sweetness. The product is suitable as a jelly exhibiting the inherent medicinal efficacies of soyasaponin.

EXAMPLE 16

"TSUKUDANI"

Two hundred and fifty g of tangle was treated to remove the sand, soaked in acid solution, and cut into squares, in usual way. Thereafter, the tangle was soaked in a mixture solution, consisting of 212 ml soy sauce, 318 ml amino acid solution, 30 g of sucrose, 20 g of corn syrup, 1 g of pullulan and 10 g of a syrup containing alpha-glycosyl soyasaponin, prepared by the method as described in EXPERIMENT 1—3 for Sample No. 4. While boiling, the mixture was added with 12 g of sodium glutamate, 8 g of caramel and 21 ml of "MIRIN'-'—a type of Japanese-style liquor, and boiled up to obtain the titled product, "TSUKUDANI"—a type of Japanese-style preserved food.

The product is an appetizing "TSUKUDANI" excellent in color, gloss and appearance, as well as in flavor and taste. The product is suitable as a "TSUKUDANI" exhibiting the inherent medicinal efficacies of soyasaponin.

EXAMPLE 17

Pickled scallion

Five kg of raw scallion was soaked in 2.5 liters of about 20% aqueous common salt solution for 3 weeks. After draining off the water, the scallion was pickled for 1 month in an acetic acid solution, consisting of 2.0 liters of water, 80 ml of glacial acetic acid and 80 g of common salt. Then, the scallion was soaked for 10 days in a seasoning solution, consisting of 800 ml of vinegar, 400 ml of "MIRIN"—a type of Japanese-style liquor, 10 g of cayenne-pepper, and 5 g of a powder containing alpha-glycosyl soyasaponin, prepared by the method as described in EXAMPLE 2, to obtain a tasty pickled scallion excellent in flavor, and exhibiting the inherent medicinal efficacies of soyasaponin.

EXAMPLE 18

Tablet

One hundred g of "SUNMALT®", trade name of a commercial crystalline maltose powder, a product of Hayashibara Co., Ltd., Okayama, Japan, 10 g of corn starch, and 10 g of a powder containing alpha-glycosyl soyasaponin, prepared by the method as described in EXAMPLE 5, were mixed, and the mixture was then shaped with the use of a tabletting machine, equipped with 20 R-punch of 12 mm diameter, into tablet of 680 mg each, 5.25 mm thick and 8±1 kg hardness.

The product is an easily administrable tablet having the inherent medicinal efficacies of soyasaponin, e.g. hypolipidemic, hypocholesterolemic or expectorant effect.

EXAMPLE 19

Dentifrice

A dentifrice was prepared by kneading a composition with a formulation of $CaHPO_4$, 45.0%; pullulan, 2.75%; sodium laulyl sulfate, 1.5%; glycerine, 18.0%; polyoxyethylene sorbitan monolaulate, 0.5%; antiseptic agent, 0.05%; "α-G-Sweet", trade name of a commercial alpha-glycosyl stevioside, product of Toyo Sugar Refining Co., Ltd., Tokyo, Japan, 0.2%; a powder containing alpha-glycosyl soyasaponin, prepared by the method as described in EXAMPLE 2, 2.0%; and water, 30.0%, in conventional manner.

The product is suitable as a dentifrice exhibiting medicinal efficacies including an expectorant effect.

EXAMPLE 20

Syrup containing alpha-glycosyl isoflavonoid

Thirty g of isoflavonoid, prepared by the method as described in EXPERIMENT 1—2, and 300 g of maltodextrin (DE 40) were dissolved together in 500 ml of a hot water. The resultant solution was adjusted to 50° C. and pH 6.0, and then added with an alpha-glucosidase solution, prepared by the method as described in EXAMPLE 1, followed by 24 hour-incubation to effect enzymatic reaction. The reaction mixture was treated similarly as in EXAMPLE 1 to obtain a syrup containing alpha-glycosyl isoflavonoid having a moisture content of 20%. The overall yield was about 90% on the basis of dry solid.

This syrup is almost free from undesirable tastes, such as bitter, astringent or lingering choky taste, but is somewhat mildly sweet. Thus, it may be ingested intact, or used in a food product.

EXAMPLE 21

Powder containing alpha-glycosyl isoflavonoid

Sixty g of isoflavonoid, prepared by the method as described in EXPERIMENT 1—2, and 180 g of beta-cyclodextrin were dissolved together in 500 ml of water while heating. The resultant solution was cooled to 50° C., adjusted to pH 5.5, and added with a cyclodextrin glucanotransferase, prepared by the method as described in EXAMPLE 2, in an amount 15 units per g beta-cyclodextrin. The solution was then incubated at 50° C. and pH 5.5 for 24 hours to effect enzymatic reaction, and the reaction mixture was treated similarly as in EXAMPLE 1 to obtain about 70 g of powder containing alpha-glycosyl isoflavonoid.

The powder containing alpha-glycosyl isoflavonoid is almost free from undesirable tastes, such as bitter, astringent or lingering choky taste. Thus, it may be ingested intact, or, if necessary, seasoned with a sweetening or souring agent prior to its use.

EXAMPLE 22

Syrup containing alpha-glycosyl isoflavonoid

Ten kg of defatted soybean was added with 25 liters of methanol, and allowed to stand at 50° C. for 3 hours to effect extraction, followed by filtration. The resultant residue was subjected twice to additional extractions using methanol similarly as above. The obtained three extracts were pooled, and concentrated in vacuo to evaporate methanol, and dried to obtain a solid. An aqueous solution of 10 w/w % of the solid was filtered, and applied on a column, packed with 8 liters of "HP-10", trade name of a commercial synthetic macroreticular resin, a product of Mitsubishi Chemical Industries Ltd., Tokyo, Japan, which was then sufficiently washed to remove impurities. To the column was charged 20 liters of methanol, and the eluate was concentrated to vacuo to evaporate methanol, dried, and pulverized to obtain about 120 g of powder containing isoflavonoid.

Fifty g of the powder and 300 g of maltodextrin (DE 30) were dissolved together in 300 ml of water, and added with 10 units of a cyclodextrin glucanotransferase per g maltodextrin, prepared by the method as described in EXPERIMENT 1—1. The mixture was incubated at pH 5.5 and 60° C. for 24 hours to effect enzymatic reaction. After inactivating the enzyme by heating, the reaction mixture was filtered, and the filtrate was concentrated to obtain a syrup containing alpha-glycosyl isoflavonoid having a moisture content of 20%. The overall yield was about 97% on the basis of dry solid.

This syrup is almost free from undesirable tastes, such as bitter, astringent, harsh or choky taste, but is somewhat mildly sweet. Thus, the syrup may be ingested intact, or used in various types of food products.

EXAMPLE 23

Syrup containing alpha-glycosyl isoflavonoid

One kg of a defatted soybean was added with 10 liters of water, kept at 50° C. for 1 hour under gentle stirring conditions, and filtered. The resultant filtrate was added with lactic acid to bring its pH to 4.5, kept at 85° C. for 10 minutes, and centrifuged to obtain a supernatant (soybean whey).

The supernatant was neutralized with an aqueous caustic soda solution to pH 7.0, added with 50 g of sucrose, 2 g of yeast extract, 8 g of $KH_2PO_4$ and 24 g of $K_2HPO_4$, kept at 100° C. for 15 minutes to effect sterilization, and cooled to prepare a culture medium. A 1% seed culture of *Leuconostoc mesenteroides* IAM 1151 was inoculated thereto, and cultured thereon at 25° C. for 24 hours. After centrifuging the culture broth, the supernatant was added with 10 g of "M-511", trade name of a commercial magnesia adsorbent, product of Hokkaido Soda Company, Ltd., Tokyo, Japan, allowed to stand for 15 minutes under gentle stirring conditions, and filtered to remove coloring impurities. Then, the filtrate was deionized by applying to ion exchange resins, "Amberlite IR-200 C (H-form)" and "Amberlite IRA-93 (OH-form)", and concentrated in vacuo to obtain about 60 g of syrup containing alpha-glycosyl isoflavonoid having a moisture content of 30%.

The alpha-glycosyl isoflavonoid constituent in this syrup was gradually hydrolyzed by isomaltodextranase (EC 3.2.1.94) into isoflavonoid and isomaltose. This confirms that one or more D-glucose residues are bound to isoflavonoid moiety in alpha-1,6 fashion in the alpha-glycosyl isoflavonoid molecule.

This syrup is almost free from undesirable tastes, such as bitter, astringent, harsh or choky taste. Thus, it may be ingested intact, or used in various types of food products.

EXAMPLE 24

Syrup containing alpha-glycosyl isoflavonoid

To 1 liter of water was added 300 g of potato starch, and 60 g of a powder containing isoflavonoid, prepared by the method as described in EXAMPLE 22, and the resultant suspension was adjusted to pH 6.0, added with a commercial saccharifying alpha-amylase (EC 3.2.1.1) of a bacterium origin, a product of Seikagaku Kogyo Co., Ltd., Tokyo, Japan, in an amount of 10 units per g starch in terms of the enzyme unit as defined in EXPERIMENT 1—1, and liquefied by heating to 80° C. under stirring conditions. After completion of the liquefaction, the resultant was cooled to 60° C., and subjected to a further enzymatic reaction for an additional 2 days. Similarly as in EXAMPLE 1, the reaction mixture was heated to inactivate the alpha-amylase, filtered, purified with a magnesia adsorbent and ion exchange resins, concentrated in vacuo, dried, and pulverized to obtain a powder containing alpha-glycosyl isoflavonoid. The overall yield was about 96% on the basis of dry solid.

This powder is almost free from undesirable tastes, such as a bitter, astringent, harsh or choky taste, but is somewhat mildly sweet. Thus, it may be ingested intact, or used in a food product.

EXAMPLE 25

Sweetener

One kg of "FUNMATSU MABIT ®", trade name of a commercial crystalline maltitol powder, available from Hayashibara Shoji, Inc., Okayama, Japan, was admixed with 30 g of "α-G-Sweet", trade name of a commercial alpha-glycosyl stevioside, a product of Toyo Sugar Refining Co., Ltd., Tokyo, Japan, and 20 g of a syrup containing alpha-glycosyl isoflavonoid, prepared by the method as described in EXAMPLE 20. The resultant admixture was placed and shaped in a mold by applying a slightly high pressure, and the content was released therefrom, and dried with a hot air to obtain a sweetener in cube, about 3 g each.

The sweetener containing alpha-glycosyl isoflavonoid is suitable for sweetening coffee, tea or soft drink and for imparting thereto the inherent medicinal efficacy of isoflavonoid, e.g. hypolipidemic or hypocholesterolemic effect. Also, the product is suitable as a low-cariogenic sweetener, as well as a low-caloric sweetener.

EXAMPLE 26

Sweetener

Fifty g of a powder containing alpha-glycosyl isoflavonoid, prepared by the method as described in EXAMPLE 21, was dissolved in 20 ml of water. The resultant solution was admixed with 1 kg of honey to obtain a sweetener containing alpha-glycosyl isoflavonoid.

This sweetener may be ingested intact, and is suitable for sweetening a health food or drink for beauty, as well as for improving the taste quality of a herb medicine.

EXAMPLE 27

Hard candy

A hard candy was prepared similarly as in EXAMPLE 8, except that the syrup containing alpha-glycosyl soyasaponin was replaced with a syrup containing alpha-glycosyl isoflavonoid, prepared by the method as described in EXAMPLE 22.

The product is suitable as a hard candy exhibiting the inherent efficacy of isoflavonoid, e.g. hypolipidemic or hypocholesterolemic effect.

EXAMPLE 28

Chewing gum

A chewing gum was prepared similarly as in EXAMPLE 10, except that the powder containing alpha-glycosyl soyasaponin was replaced with a powder containing alpha-glycosyl isoflavonoid, prepared by the method as described in EXAMPLE 24.

Since the product is excellent in texture and sweetness, it is suitable as a chewing gum exhibiting the inherent medicinal efficacy of isoflavonoid, e.g. hypolipidemic or hypocholesterolemic effect. Also, the product is suitable as a low-caloric or low-cariogenic chewing gum.

EXAMPLE 29

Chocolate

A chocolate was prepared similarly as in EXAMPLE 11, except that the powder containing alpha-glycosyl soyasaponin was replaced with a powder containing alpha-glycosyl isoflavonoid, prepared by the method as described in EXAMPLE 21.

The product is excellent in texture and flavor, and free from fat- or sugar-blooming during storage. The product is suitable as a chocolate exhibiting the inherent medicinal efficacy of isoflavonoid, e.g. hypolipidemic or hypocholesterolemic effect.

EXAMPLE 30

Sour milk beverage

A sour milk beverage was prepared similarly as in EXAMPLE 12, except that the syrup containing alpha-glycosyl soyasaponin was replaced with a syrup containing alpha-glycosyl isoflavonoid, prepared by the method as described in EXAMPLE 23.

The product is suitable as a sour milk beverage exhibiting the inherent medicinal efficacies of isoflavonoid.

EXAMPLE 31

Carbonated beverage

A carbonated beverage was prepared in the same manner as in EXAMPLE 13, except that a syrup containing alpha-glycosyl isoflavonoid, prepared by the method as described in EXAMPLE 22, was replaced for the syrup containing alpha-glycosyl soyasaponin.

The product is suitable as a health drink exhibiting the inherent medicinal efficacies of isoflavonoid.

EXAMPLE 32

Jelly

A jelly was prepared by the method as described in EXAMPLE 14, except that the syrup containing alpha-glycosyl soyasaponin was replaced with a syrup containing alpha-glycosyl isoflavonoid, prepared by the method as described in EXAMPLE 22.

The product is excellent in biting properties. The product is suitable as a jelly exhibiting the inherent medicinal efficacies of isoflavonoid.

EXAMPLE 33

Jelly

A jelly was prepared similarly as in EXAMPLE 15, except that a syrup containing alpha-glycosyl isoflavonoid, prepared by the method as described in EXAMPLE 22, was used in place of the syrup containing alpha-glycosyl soyasaponin.

The product is a jelly having a refreshing taste and sweetness. The product is suitable as a jelly exhibiting the inherent medicinal efficacies of isoflavonoid.

EXAMPLE 34

"TSUKUDANI"

The titled product was prepared similarly as in EXAMPLE 16, except that a syrup containing alpha-glycosyl isoflavonoid, prepared by the method as described in EXPERIMENT 1—3, was used in place of the syrup containing alpha-glycosyl soyasaponin.

The product is an appetizing "TSUKUDANI" excellent color, gloss and appearance, as well as in flavor and taste. The product is suitable as a "TSUKUDANI" exhibiting the inherent medicinal efficacies of isoflavonoid.

EXAMPLE 35

Pickled scallion

The titled product was obtained similarly as in EXAMPLE 17, except that a syrup containing alpha-glycosyl isoflavonoid, prepared by the method as described in EXAMPLE 21, was used in place of the syrup containing alpha-glycosyl soyasaponin.

The product is a tasty pickled scallion excellent in flavor, and exhibiting the inherent medicinal efficacies of isoflavonoid.

EXAMPLE 36

Tablet

Tablets of 680 mg each, 5.25 mm thick and 8±1 kg hardness were prepared similarly as in EXAMPLE 18, except that a powder containing alpha-glycosyl isoflavonoid, prepared by the method as described in EXAMPLE 24, was replaced for the powder containing alpha-glycosyl soyasaponin.

The product is an easily administrable tablet having the inherent medicinal efficacies of isoflavonoid, e.g. hypolipidemic, hypocholesterolemic or expectorant effect.

EXAMPLE 37

Dentifrice

A dentifrice was prepared similarly as in EXAMPLE 19, except that a powder containing alpha-glycosyl isoflavonoid, prepared by the method as described in EXAMPLE 21 was replaced for the powder containing alpha-glycosyl soyasaponin.

The product is suitable as a dentifrice exhibiting antihaemolytic or antibacterial effects.

While specific details have been shown and described, it should be understood that changes and alterations may be resorted to without departing from the spirit of the invention as defined in the appended claims.

We claim:

1. A process for producing alpha-glycosyl soybean glycoside or a mixture containing same, which process comprises:
   providing an aqueous solution containing a soybean glycoside and an alpha-glucosyl saccharide; and
   subjecting the solution to an alpha-glucosyl transferase.

2. A process as set forth in claim 1, wherein said alpha-glucosyl transferase is a member selected from the group consisting of alpha-glucosidase, alpha-amylase, cyclodextrin glucanotransferase, dextransucrase, dextran dextrinase and amylosucrase.

3. A process as set forth in claim 1, which process comprises:
   providing an aqueous solution containing a soybean glycoside and an alpha-glucosyl saccharide;
   subjecting the solution to an alpha-glucosyl transferase under the conditions sufficient to effect a substantial enzymatic transferring reaction; and
   recovering the resultant alpha-glycosyl soybean glycoside.

4. A process as set forth in claim 1, wherein said alpha-glucosyl saccharide is a member selected from the group consisting of gelatinized starch, liquefied starch, partial starch hydrolysate, maltose, maltotriose, maltotetraose, sucrose and mixture thereof.

5. A process as set forth in claim 4, wherein the DE of the gelatinized starch, liquefied starch or partial starch hydrolysate is up to 60.

6. A process as set forth in claim 1, which process comprises:
   providing an aqueous solution containing 0.01–30 w/w % soybean glycoside and 1–50 w/w % alpha-glucosyl saccharide; and
   subjecting the solution to an alpha-glucosyl transferase at a pH in the range of 3–10 and a temperature in the range of 20°–80° C. for a period sufficient to form a substantial amount of alpha-glycosyl soybean glycoside.

7. A process as set forth in claim 1, wherein the weight ratio of soybean glycoside to alpha-glucosyl saccharide is in the range of 0.5–500 on the basis of dry solid.

8. A process as set forth in claim 1, wherein said soybean glycoside is a member selected from the group consisting of soyasaponin, isoflavonoid and mixture thereof.

9. A process as set forth in claim 1, wherein a soybean milk is used as the source for soybean glycoside.

10. An orally-usable composition which contains an alpha-glycosyl soybean glycoside.

11. A composition as set forth in claim 10, which is in the form of paste.

12. A composition as set forth in claim 10, which is in the form of solid.

13. A composition as set forth in claim 10, wherein said alpha glycosyl soybean glycoside is prepared by
   providing an aqueous solution containing a soybean glycoside and an alpha-glucosyl saccharide; and
   subjecting the solution to an alpha-glucosyl transferase.

14. A composition as set forth in claim 10, which is a member selected from the group consisting of food, drink, pet food, feed, cosmetics, drug and tobacco.

15. A composition as set forth in claim 10, which additionally contains soybean glycoside and alpha-glucosyl saccharide.

16. A composition as set forth in claim 10, wherein said alpha-glycosyl soybean glycoside is a member selected from the group consisting of alpha-glycosyl soyasaponin, alpha-glycosyl isoflavonoid and mixture thereof.

17. The composition of claim 10 which is in the form of a food product.

18. Alpha-glycosyl soybean glycoside, which has a chemical structure wherein one or more alpha-glucosyl residues are bound to a soybean glycoside moiety in alpha-fashion.

19. Alpha-glycosyl soybean glycoside as set forth in claim 18, wherein said soybean glycoside is a member selected from the group consisting of soyasaponin, isoflavonoid and mixture thereof.

20. A process for producing food product, said process comprises:
   incorporating a substantial amount of alpha-glycosyl soybean glycoside into a food product.

21. A process as set forth in claim 20, wherein said food product is a food or drink.

22. A process as set forth in claim 20, wherein said food product is a member selected from the group consisting of pet food, feed, tobacco, cosmetic or drug.

23. A process as set forth in claim 20, wherein said food product is in the form of liquid.

24. A process as set forth in claim 20, wherein said food product is in the form of paste.

25. A process as set forth in claim 20, wherein said food product is in the form of solid.

26. A process as set forth in claim 20, wherein said alpha-glycosyl soybean glycoside is obtained by
   providing an aqueous solution containing a soybean glycoside and an alpha-glucosyl saccharide; and
   subjecting the solution to an alpha-glucosyl transferase.

27. A process as set forth in claim 20, wherein said alpha-glycosyl soybean glycoside is a member selected from the group consisting of alpha-glycosyl soyasaponin, alpha-glycosyl isoflavonoid and mixture thereof.

28. In an orally-usable composition wherein a soybean glycoside is incorporated, the improvement whereby the taste quality of the composition is extremely improved, comprising partially or completely replacing the soybean glycoside with its alpha-glycosyl derivative.

29. The improved orally-usable composition of claim 28, wherein said orally usable composition is a food product.

30. A method for purifying alpha-glycosyl soybean glycoside, said method containing the steps of:
   providing an aqueous solution of alpha-glycosyl soybean glycoside wherein impurities are present;
   allowing the solution to contact with a magnesia adsorbent thereby to adsorb the impurities thereon; and
   recovering the alpha-glycosyl soybean glycoside from the resultant non-adsorbed part.

31. A method as set forth in claim 30, wherein said alpha-glycosyl soybean glycoside is a member selected from the group consisting of alpha-glycosyl soyasaponin, alpha-glycosyl isoflavonoid and mixture thereof.

32. A method for recovering alpha-glycosyl soybean glycoside form its mixture with alpha-glucosyl saccharide, said method containing the steps of:

providing an aqueous solution containing alpha-glycosyl soybean glycoside and alpha-glucosyl saccharide;

allowing the solution to contact with a synthetic macroreticular resin thereby to adsorb the alpha-glycosyl soybean glycoside thereon;

allowing the resin to contact with a low alcohol solution; and recovering the alpha-glycosyl soybean glycoside from the eluate.

33. A method as set forth in claim 32, wherein said alpha-glycosyl soybean glycoside is a member selected from the group consisting of alpha-glycosyl soyasaponin, alpha-glycosyl isoflavonoid and mixture thereof.

* * * * *